US00PP18480P2

(12) United States Plant Patent
Dümmen

(10) Patent No.: US PP18,480 P2
(45) Date of Patent: Feb. 12, 2008

(54) ***GERANIUM* PLANT NAMED 'DUEVINEON'**

(50) Latin Name: *Pelargonium×hortorum*
Varietal Denomination: Duevineon

(75) Inventor: Marga Dümmen, Rheinberg (DE)

(73) Assignee: Dümmen Jungpflanzen GbR, Rheinberg (DE)

( * ) Notice: Subject to any disclaimer, the term of this patent is extended or adjusted under 35 U.S.C. 154(b) by 90 days.

(21) Appl. No.: 11/349,643

(22) Filed: Feb. 7, 2006

(51) Int. Cl.
*A01H 5/00* (2006.01)

(52) U.S. Cl. ..... Plt./329
(58) Field of Classification Search ..... Plt./329
See application file for complete search history.

(56) References Cited

U.S. PATENT DOCUMENTS

PP11,440 P * 7/2000 Trees ..... Plt./329
PP15,858 P2 * 7/2005 Dummen ..... Plt./329

OTHER PUBLICATIONS

UPOV ROM GTITM Computer Database 2006/05 Citation for 'Duevineon'.*

* cited by examiner

*Primary Examiner*—Wendy Haas
(74) *Attorney, Agent, or Firm*—C. A. Whealy

(57) ABSTRACT

A new and distinct cultivar of Zonal *Geranium* plant named 'Duevineon', characterized by its upright, somewhat outwardly spreading and rounded plant habit; vigorous growth habit; freely branching habit; freely and early flowering habit; and red purple-colored double flowers.

1 Drawing Sheet

Botanical denomination: *Pelargonium×hortorum.*
Cultivar designation: 'Duevineon'.

BACKGROUND OF THE INVENTION

The present invention relates to a new and distinct cultivar of Zonal *Geranium* plant, botanically known as *Pelargonium×hortorum,* and hereinafter referred to by the name 'Duevineon'.

The new Zonal *Geranium* is a product of a planned breeding program conducted by the Inventor in Rheinberg, Germany. The objective of the breeding program was to develop new freely and early flowering Zonal *Geraniums* with attractive flower and foliage colors.

The new Zonal *Geranium* originated from a cross-pollination made by the Inventor on Jul. 1, 2002, of a proprietary selection of *Pelargonium×hortorum* identified as code number F-01-22, not patented, as the female, or seed, parent with a proprietary selection of *Pelargonium×hortorum* identified as code number S-01-26, not patented, as the male, or pollen, parent. The cultivar 'Duevineon' was discovered and selected by the Inventor as a flowering plant within the progeny from this cross-pollination in a controlled environment in Rheinberg, Germany on Jun. 1, 2004.

Asexual reproduction of the new cultivar by terminal vegetative cuttings at Rheinberg, Germany since Jul. 1, 2004, has shown that the unique features of this new Zonal *Geranium* are stable and reproduced true to type in successive generations of asexual reproduction.

SUMMARY OF THE INVENTION

The following traits have been repeatedly observed and are determined to be the unique characteristics of 'Duevineon'. These characteristics in combination distinguish 'Duevineon' as a new cultivar and distinguish it from other known Zonal *Geranium* cultivars:

1. Upright, outwardly spreading and rounded plant habit.
2. Vigorous growth habit.
3. Freely branching habit.
4. Freely and early flowering habit.
5. Red purple-colored double flowers.

Compared to plants of the female parent selection, plants of the new Zonal *Geranium* are more vigorous and more freely branching. Compared to plants of the male parent selection, plants of the new Zonal *Geranium* are more vigorous than plants of the male parent selection. In addition, plants of the new Zonal *Geranium* and the male parent selection differ in flower color as plants of the male parent selection have more blue-colored flowers.

The new Zonal *Geranium* can be compared to plants of the cultivar Dueazulia, disclosed in U.S. Plant Pat. No. 15,858. In side-by-side comparisons conducted in Rheinberg, Germany, plants of the new Zonal *Geranium* differed from plants of the cultivar Dueazulia in the following characteristics:

1. Plants of the new Zonal *Geranium* were more vigorous than plants of the cultivar Dueazulia.
2. Plants of the new Zonal *Geranium* and the cultivar Dueazulia differed in leaf color as plants of the cultivar Dueazulia have more blue-colored flowers.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Flower and foliage colors in the photograph may differ slightly from the color values cited in the detailed botanical description which accurately describe the colors of the new Zonal *Geranium*. The photograph comprises a side perspective view of a typical flowering plant of 'Duevineon' grown in a container.

DETAILED BOTANICAL DESCRIPTION

The cultivar 'Duevineon' has not been observed under all possible environmental conditions. The phenotype may vary somewhat with variations in environment, such as temperature and light intensity, without, however, any variance in genotype.

The aforementioned photograph, following observations and measurements describe plants grown in Rheinberg, Germany during the summer under commercial practice in a glass-covered greenhouse with day and night temperatures about 18° C. and light levels about 4,500 foot-candles. Plants were grown in 10.5-cm containers. Plants were pinched once about three weeks after planting. Plants were about eight weeks from unrooted cuttings when the photograph and the detailed botanical description were taken. In the following description, color references are made to The Royal Horticultural Society Colour Chart, 1995 edition, except where general terms of ordinary dictionary significance are used.

Botanical classification: *Pelargonium×hortorum* cultivar 'Duevineon'.

Parentage:

*Female parent.*—Proprietary selection of *Pelargonium×hortorum* identified as F-01-22, not patented.

*Male parent.*—Proprietary selection of *Pelargonium×hortorum* identified as S-01-26, not patented.

Propagation:

*Type cutting.*—Terminal vegetative cuttings.

*Time to initiate roots, summer.*—About 5 days at 20° C.

*Time to initiate roots, winter.*—About 7 days at 20° C.

*Time to develop roots, summer.*—About three weeks at 20° C.

*Time to develop roots, winter.*—About four weeks at 20° C.

*Root description.*—Fine, fibrous; white in color.

*Rooting habit.*—Freely branching.

Plant description:

*General appearance.*—Upright, somewhat outwardly spreading and rounded plant habit; densely foliated.

*Growth and branching habit.*—Vigorous growth habit. Freely branching, about three to five lateral branches per plant.

*Plant height.*—About 24 cm.

*Plant width.*—About 21 cm.

*Lateral branches.*—Length: About 8 cm. Internode length: About 1.4 cm. Texture: Smooth, glabrous. Color: 144A.

*Foliage description.*—Arrangement: Alternate, simple. Length: About 6.1 cm. Width: About 7.6 cm. Shape: Reniform. Apex: Rounded. Base: Cordate. Margin: Crenate. Venation pattern: Palmate. Texture, upper and lower surfaces: Smooth, glabrous. Color: Developing and fully expanded foliage, upper surface: 137A to 137B; venation, 144A. Developing and fully expanded foliage, lower surface: 138B; venation, 144A. Zonation pattern: Not visible. Petiole: Length: About 6.6 cm. Diameter: About 2 mm. Texture, upper and lower surfaces: Smooth. Color, upper and lower surfaces: 144A.

Flower description:

*Flower arrangement.*—Red purple-colored double flowers arranged in rounded hemispherical umbels arising from apical leaf axils. Umbels displayed above and beyond the foliage on peduncles. Flowers rounded in form. Umbels persistent, flowers not persistent. Flowers not fragrant.

*Quantity of flowers.*—Freely flowering; at full flower, plants have about six flower umbels with about 25 to 30 flowers per umbel.

*Flowering season.*—Flowering continuous spring through the summer. Plants begin flowering about eight weeks after planting.

*Flower longevity.*—Flowers last about five to seven days on the plant.

*Umbel size.*—Diameter: About 11.2 cm. Height: About 6.2 cm.

*Flower size.*—Diameter: About 3.8 cm. Depth (height): About 1.9 cm.

*Flower buds.*—Length: About 1.6 cm. Diameter: About 7 mm. Shape: Ovoid. Color: 144A.

*Petals.*—Quantity per flower: About five. Length: About 2.6 cm. Width: About 2.5 cm. Shape: Obovate. Apex: Rounded. Base: Attenuate. Margin: Entire; sinuate. Texture, upper and lower surfaces: Smooth. Color: When opening and fully opened, upper surface: 61B; towards the apex, 43A; color does not fade with development. When opening and fully opened, lower surface: 61B to 61C.

*Petaloids.*—Quantity per flower: Zero to about three. Length: About 2.2 cm. Width: About 1.4 cm. Shape: Obovate. Apex: Rounded. Base: Attenuate. Margin: Entire; sinuate. Texture, upper and lower surfaces: Smooth. Color: When opening and fully opened, upper surface: 61B; towards the apex, 43A. When opening and fully opened, lower surface: 61B to 61C.

*Sepals.*—Quantity per flower: About five arranged in a single whorl. Length: About 1 cm. Width: About 3.4 mm. Shape: Elongated, tapering. Apex: Apiculate. Margin: Entire. Texture, upper and lower surfaces: Smooth; glabrous. Color, upper and lower surfaces: 144A.

*Peduncle* (*umbel stem*).—Length: About 15.3 cm. Diameter: About 1.5 cm. Angle: Mostly erect. Strength: Moderately strong. Texture: Smooth; glabrous. Color: 144A.

*Pedicel* (*individual flower stem*).—Length: About 2.5 cm. Diameter: About 1 mm. Angle: Mostly erect. Strength: Moderately strong. Texture: Pubescent. Color: 59B.

*Reproductive organs.*—Androecium: Anther quantity per flower: About ten. Anther length: About 2 mm. Anther shape: Ovate. Anther color: 47C. Pollen amount: Moderate. Pollen color: 28A. Gynoecium: Pistil quantity per flower: One. Pistil length: About 1.1 cm. Stigma shape: Five-parted, star-shaped. Stigma color: 46A. Style length: About 2.5 mm. Style color: 46A. Ovary color: Close to 144A.

*Seed/fruit.*—Development of seeds and fruit have not been observed.

Disease/pest resistance: Plants of the new Zonal *Geranium* have not been observed to be resistant to pathogens and pests common to Zonal *Geraniums*.

Temperature tolerance: Plants of the new Zonal *Geranium* have been observed to be tolerant to temperatures ranging from about 5° C. to about 40° C.

It is claimed:

1. A new and distinct cultivar of Zonal Geranium plant named 'Duevineon', as herein illustrated and described.

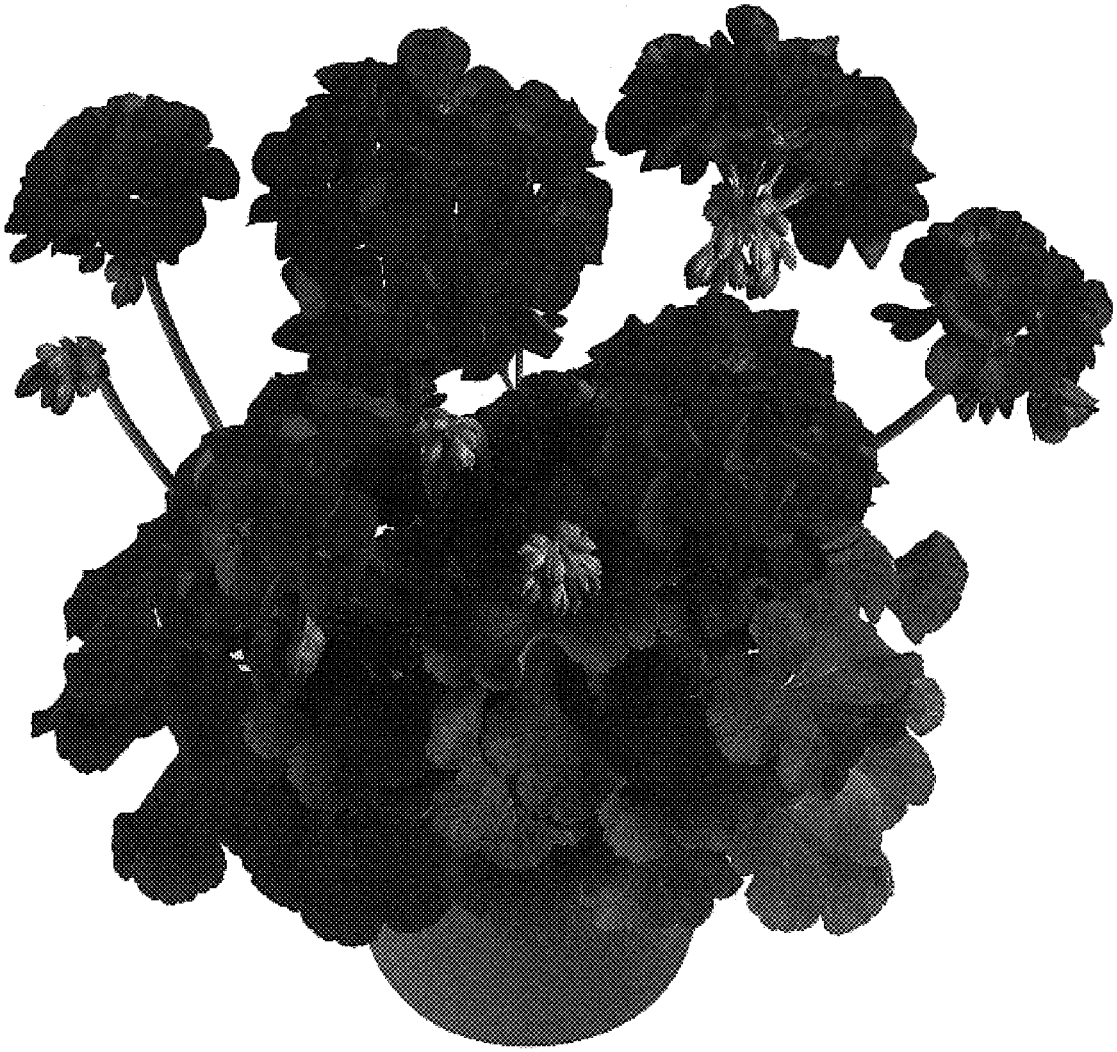

* * * * *